United States Patent
Gullberg et al.

(10) Patent No.: US 12,398,449 B2
(45) Date of Patent: Aug. 26, 2025

(54) DUPLEX STAINLESS STEEL AND FORMED OBJECT THEREOF

(71) Applicant: Alleima Tube AB, Sandviken (SE)

(72) Inventors: Daniel Gullberg, Gavle (SE); Christina Haraldsson, Sandviken (SE); Anders Wilson, Gavle (SE); Alexander Scheerder, Sittard (NL); Kirk Ofei, Sittard (NL)

(73) Assignee: Alleima Tube AB, Sandviken (SE)

( * ) Notice: Subject to any disclaimer, the term of this patent is extended or adjusted under 35 U.S.C. 154(b) by 0 days.

(21) Appl. No.: 18/407,928

(22) Filed: Jan. 9, 2024

(65) Prior Publication Data

US 2024/0141466 A1    May 2, 2024

Related U.S. Application Data

(63) Continuation of application No. 17/556,607, filed on Dec. 20, 2021, now abandoned, which is a continuation of application No. 15/746,006, filed as application No. PCT/EP2016/067323 on Jul. 20, 2016, now Pat. No. 11,242,584.

(30) Foreign Application Priority Data

Jul. 20, 2015 (EP) .................................... 15177437

(51) Int. Cl.
| | | |
|---|---|---|
| C22C 38/00 | (2006.01) | |
| B01D 3/32 | (2006.01) | |
| B01J 19/02 | (2006.01) | |
| C07C 273/04 | (2006.01) | |
| C21D 6/00 | (2006.01) | |
| C21D 8/00 | (2006.01) | |
| C21D 9/08 | (2006.01) | |
| C22C 33/02 | (2006.01) | |
| C22C 33/04 | (2006.01) | |
| C22C 38/02 | (2006.01) | |
| C22C 38/04 | (2006.01) | |
| C22C 38/42 | (2006.01) | |
| C22C 38/44 | (2006.01) | |
| C22C 38/58 | (2006.01) | |
| F28F 21/08 | (2006.01) | |
| B22F 3/15 | (2006.01) | |
| C21D 8/10 | (2006.01) | |

(52) U.S. Cl.
CPC .............. *C22C 38/44* (2013.01); *B01D 3/32* (2013.01); *B01J 19/02* (2013.01); *C07C 273/04* (2013.01); *C21D 6/004* (2013.01); *C21D 8/005* (2013.01); *C21D 9/08* (2013.01); *C22C 33/0285* (2013.01); *C22C 33/04* (2013.01); *C22C 38/001* (2013.01); *C22C 38/002* (2013.01); *C22C 38/02* (2013.01); *C22C 38/04* (2013.01); *C22C 38/42* (2013.01); *C22C 38/58* (2013.01); *F28F 21/083* (2013.01); *B01J 2219/0286* (2013.01); *B22F 3/15* (2013.01); *C21D 8/105* (2013.01); *C21D 2211/001* (2013.01); *C21D 2211/005* (2013.01); *Y02P 10/122* (2015.11)

(58) Field of Classification Search
CPC ..... C22C 38/44; C22C 38/001; C22C 38/002; C22C 38/02; C22C 38/04; C22C 38/42
USPC ........................................................ 428/581
See application file for complete search history.

(56) References Cited

U.S. PATENT DOCUMENTS

| | | |
|---|---|---|
| 5,284,530 A | 2/1994 | Azuma et al. |
| 5,582,656 A | 12/1996 | Kangas et al. |
| 6,312,532 B1 | 11/2001 | Kangas et al. |
| 7,341,903 B2 | 3/2008 | Hohage et al. |
| 10,184,160 B2 | 1/2019 | Sawawatari et al. |
| 2008/0138232 A1 | 6/2008 | Kangas et al. |
| 2010/0084121 A1 | 4/2010 | Kivisäkk et al. |
| 2015/0107724 A1 | 4/2015 | Sawawatari et al. |
| 2018/0195158 A1 | 7/2018 | Gullberg et al. |

FOREIGN PATENT DOCUMENTS

| | | |
|---|---|---|
| CA | 2934867 A1 | 7/2015 |
| EP | 0534864 A1 | 3/1993 |
| EP | 1340829 A1 | 9/2003 |
| EP | 1688511 A1 | 8/2006 |
| EP | 2801396 A1 | 11/2014 |
| JP | 62-230495 A | 10/1987 |
| JP | H08-5118229 A | 12/1996 |
| JP | 2003-503596 A | 1/2003 |
| JP | 2003-301241 A | 10/2003 |

(Continued)

OTHER PUBLICATIONS

Priority Application of EP 15177441.

(Continued)

*Primary Examiner* — Katherine A Christy
(74) *Attorney, Agent, or Firm* — Morgan, Lewis & Bockius LLP

(57) ABSTRACT

A corrosion resistant duplex stainless steel (ferritic austenitic alloy) is suitable for use in a plant for the production of urea. Uses of the corrosion resistant duplex stainless steel include in objects made of said duplex stainless steel, in methods for the production of urea, in a plant for the production of urea comprising one or more parts made from said duplex stainless steel, and in methods of modifying an existing plant for the production of urea. In one aspect, the composition consists of in weight % (wt %): C 0.010 to 0.015; S 0.08 to 0.23; Mn 1.0 to 1.05; Cr 29.07 to 29.92; Ni 5.76 to 7.17; Mo 3.0 to 4.0; W max 2.55; N 0.3 to 0.35; Cu max 0.01; S max 0.008; P max 0.008; at least one of Ti, Nb, Hf, Ca, Ba, V, and B max 0.5 total; balance Fe and unavoidable occurring impurities.

5 Claims, No Drawings

(56) References Cited

FOREIGN PATENT DOCUMENTS

| JP | 2010-513708 A | 4/2010 |
|---|---|---|
| JP | 5500324 B1 | 5/2014 |
| KR | 10-0314232 B1 | 12/2001 |
| KR | 10-2007-0073870 A | 7/2007 |
| WO | 9500674 A1 | 1/1995 |
| WO | 03020994 A1 | 3/2003 |
| WO | 2006/049572 A1 | 5/2006 |
| WO | 2008/073047 A1 | 6/2008 |
| WO | 2014/034522 A1 | 3/2014 |
| WO | 2015/097253 A1 | 7/2015 |
| WO | 2015/099530 A1 | 7/2015 |
| WO | 2017/013180 A1 | 1/2017 |

OTHER PUBLICATIONS

Priority Application of EP15177437.
Notice of Opposition dated Sep. 24, 2020 in EP Application No. EP 16757366.6
Notice of Reasons for Rejection dated Feb. 12, 2020 issued in Japanese Patent Application No. 2018-502633.
Article 94(3) Communication issued Feb. 16, 2021 in European Patent Application No. 16741626.2.
Ullmann's Encyclopedia of Industrial Chemistry, vol. A27: Thorium and Thorium Compounds to Vitamins, 1996, pp. 333-350.
Office Action dated Apr. 11, 2024, issued in corresponding Chinese Patent Application No. 202310052481.X.

DUPLEX STAINLESS STEEL AND FORMED OBJECT THEREOF

RELATED APPLICATION DATA

This application is a continuation application of U.S. application Ser. No. 17/556,607 filed Dec. 20, 2021, which is continuation application of U.S. application Ser. No. 15/746,006 filed Jan. 19, 2018, which is a § 371 National Stage Application of PCT International Application No. PCT/EP2016/067323 filed Jul. 20, 2016 claiming priority to EP 15177437.9 filed Jul. 20, 2015, the entire content of each of these applications is incorporated herein by reference.

TECHNICAL FIELD

The present disclosure relates to a corrosion resistant duplex stainless steel (ferritic austenitic alloy) which is suitable for use in a plant for the production of urea. The disclosure also relates to objects made of said duplex stainless steel and uses of the duplex stainless steel. Furthermore, the present disclosure also relates to a method for the production of urea and to a plant for the production of urea comprising one or more parts made from said duplex stainless steel, and to a method of modifying an existing plant for the production of urea.

BACKGROUND

Duplex stainless steel refers to ferritic-austenitic alloy. Such alloys have a microstructure comprising ferritic and austenitic phases. Background references in this respect include WO 95/00674 and U.S. Pat. No. 7,347,903. The duplex stainless steels described therein are highly corrosion resistant and can therefore be used, e.g., in the highly corrosive environment of a urea manufacturing plant.

Urea and the Production Thereof

Urea ($NH_2CONH_2$) may be produced from ammonia and carbon dioxide at elevated temperature (typically between 150° C. and 250° C.) and pressure (typically between 12 and 40 MPa) in the urea synthesis section of a urea plant. In this synthesis, two consecutive reaction steps can be considered to take place. In the first step, ammonium carbamate is formed, and in the next step, this ammonium carbamate is dehydrated so as to provide urea. The first step (i) is exothermic, and the second step can be represented as an endothermic equilibrium reaction (ii):

In a typical urea production plant, the foregoing reactions are conducted in a urea synthesis section so as to result in an aqueous solution comprising urea. In one or more subsequent concentration sections, this solution is concentrated to eventually yield urea in the form of a melt rather than a solution. This melt is further subjected to one or more finishing steps, such as prilling, granulation, pelletizing or compacting.

A frequently used process for the preparation of urea according to a stripping process is the carbon dioxide stripping process, as for example described in Ullmann's Encyclopedia of Industrial Chemistry, Vol. A27, 1996, pp. 333-350. In this process, the synthesis section is followed by one or more recovery sections. The synthesis section comprises a reactor, a stripper, a condenser and, preferably but not necessarily, a scrubber in which the operating pressure is in the range of from 12 to 18 MPa, such as in from 13 to 16 MPa.

In the synthesis section, the urea solution leaving the urea reactor is fed to a stripper in which a large amount of non-converted ammonia and carbon dioxide is separated from the aqueous urea solution.

Such a stripper can be a shell- and tube-heat exchanger in which the urea solution is fed to the top part at the tube side and a carbon dioxide feed, for use in urea synthesis, is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide, inert gases and a small amount of water.

Said vapor is typically condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The formed solution, which contains condensed ammonia, carbon dioxide, water and urea, is recirculated together with the non-condensed ammonia, carbon dioxide and inert vapor.

The processing conditions are highly corrosive, particularly due to the hot and concentrated carbamate solution. In order to try to prevent corrosion, oxygen, typically in the form of passivation air has been added to the urea process as a passivation agent, i.e. part of the oxygen will together with the chromium in the steel form a protective chromium oxide layer on the stainless steel surfaces of the equipment.

In the past, the corrosion presented a problem in the sense that the urea manufacturing equipment, even though made from stainless steel and even though passivation air was added, would corrode quite fast and be prone to early replacement and also because presence of oxygen presents an inherently unsafe situation. This has been resolved, particularly by making the equipment, i.e. the relevant parts thereof subjected to the mentioned corrosive conditions, from a duplex stainless steel, and more specifically the so called super duplex stainless steel as described in WO 95/00674 (which is sold under the trademark Safurex®). This super duplex stainless steel has an increased content of chromium, as the combination of oxygen and the duplex steel has allowed a significant reduction of the amount of oxygen to be needed for passivation and a lower level of passive corrosion. Thus, the super duplex stainless steels which are used in carbamate environment, e.g. in plants for the production of urea, work very well but at high temperatures, i.e. where the temperature is higher than 200° C., for example at 205° C., the level of passive corrosion may be higher than desired. Hence, there is still a need for a more corrosion resistant duplex stainless steel which will increase the lifetime of specific equipment of a plant for the production of urea operated at higher temperatures, such as for instance the HP (high pressure) Stripper.

Furthermore, another problem of the use of duplex stainless steels is that the original microstructure, i.e. the microstructure that the duplex stainless steel had when it was produced by the steel manufacturer, may change when the duplex stainless steel is further processed, for example by welding. The microstructural stability of the duplex stainless steel is dependent on the composition and when complicated parts are manufactured, it is important to have a material which microstructure is stable during working in order to assure proper corrosion resistance as well as sufficient mechanical properties. Thus, there is also a need for a duplex stainless steel having a stable microstructure.

Hence, there still exists a need for a further improvement of the duplex stainless steel materials used in the plants for the production of urea, especially for those parts which are exposed to high temperatures and corrosive fluids, such as the stripper tubes (the tubes of the stripper).

It is therefore desired to provide a corrosion resistant material having an improved passive corrosion rate, especially when exposed to fluids comprising carbamate at high temperatures, such as for example in the stripper tubes, to thereby prolong the life time of the stripper tubes and at the same time have good enough structure stability of the materials of the stripper and more specific the structure stability in the heat affected zones of the welds connecting the heat exchanger tubes to the tubesheet.

SUMMARY OF THE DISCLOSURE

In order to address one or more of the foregoing desires, the present disclosure, in one aspect, provides a duplex stainless steel comprising in weight % (wt %):

| | |
|---|---|
| C | max 0.030; |
| Si | max 0.8; |
| Mn | max 2.0; |
| Cr | 29.0 to 31.0; |
| Ni | 5.0 to 9.0; |
| Mo | less than 4.0; |
| W | less than 4.0; |
| N | 0.25-0.45; |
| Cu | max 2.0; |
| S | max 0.02; |
| P | max 0.03; | balance Fe and unavoidable occurring impurities; and
wherein the content of Mo+W is greater than 3.0 but less than 4.0.

In the present disclosure, the terms "carbamate" and "ammonium carbamate" are used interchangeably. Ammonium carbamate is preferred as carbamate.

Additionally, the present disclosure relates to the use of a duplex stainless steel in carbamate environment, the duplex stainless steel comprising in weight % (wt %):

| | |
|---|---|
| C | max 0.030; |
| Si | max 0.8; |
| Mn | max 2.0; |
| Cr | 29.0 to 31.0; |
| Ni | 5.0 to 9.0; |
| Mo | less than 5.0; |
| W | less than 5.0; |
| N | 0.25 to 0.45; |
| Cu | max 2.0; |
| S | max 0.02; |
| P | max 0.03; | balance Fe and unavoidable occurring impurities; and
wherein the content of Mo+W is greater than 3.0 but less than 4.0.

Furthermore, the present disclosure relates to formed objects of the hereinabove or hereinafter defined duplex stainless steel and to the use of the stainless steel as defined hereinabove or hereinafter in a plant for the production of urea.

The present disclosure relates also to a method for producing urea wherein at least one part of the equipment is made from a duplex stainless steel as defined hereinabove or hereinafter and a plant for the production of urea comprising one or more parts comprising a duplex stainless steel as defined hereinabove or hereinafter.

Further, the present disclosure also provides a method of modifying an existing plant for the production of urea and a method for reducing the passive corrosion rate of a urea plant by using a duplex stainless steel as defined the hereinabove or hereinafter.

DETAILED DESCRIPTION

The present disclosure relates to a duplex stainless steel comprising in weight % (wt %):

| | |
|---|---|
| C | max 0.030; |
| Si | max 0.8; |
| Mn | max 2.0; |
| Cr | 29.0 to 31.0; |
| Ni | 5.0 to 9.0; |
| Mo | less than 4.0; |
| W | less than 4.0; |
| N | 0.25-0.45; |
| Cu | max 2.0; |
| S | max 0.02; |
| P | max 0.03; | balance Fe and unavoidable occurring impurities; and
wherein the content of Mo+W is greater than 3.0 but less than 4.0.

Thus, e.g., the present disclosure relates to a duplex stainless steel comprising in weight % (wt %):

| | |
|---|---|
| C | max 0.020; |
| Si | max 0.8; |
| Mn | max 2.0; |
| Cr | 29.0 to 31.0; |
| Ni | 5.0 to 9.0; |
| Mo | less than 4.0; |
| W | less than 4.0; |
| N | 0.25 to 0.45; |
| Cu | max 2.0; |
| S | max 0.01; |
| P | max 0.02; | balance Fe and unavoidable occurring impurities; and
wherein the content of Mo+W is greater than 3.0 but less than 4.0.

In a broad sense, the present disclosure is based on the judicious insight that even better corrosion resistance is obtained with the duplex stainless steel as defined hereinabove or hereinafter for those areas which are exposed to carbamate at high pressure and high temperature. Thus, said duplex stainless steel is especially useful for manufacturing parts which are exposed to concentrated ammonium carbamate at high temperature (more than about 180° C.), such as parts of the heat exchanger tubes and/or, or for example, tubes in strippers. Even though the super duplex stainless steel as described in WO 95/00674 has excellent corrosion resistance in carbamate solutions (even at zero oxygen) up to a temperature of more than 180° C., the passive corrosion rate of the duplex stainless steel leaves room for improvement especially at temperatures above about 180° C. (prevailing in the stripper tubes). The duplex stainless steel as defined hereinabove or hereinafter shows remarkably lower passive corrosion rates at these extreme temperatures. One of the advantages of the duplex stainless steel is that it provides for improved life time expectancy of the stripper, in particular of the heat exchange tubes.

The present disclosure also relates to the use in carbamate environment, such as ammonium carbamate environment, of the duplex stainless steel as defined hereinabove or hereinafter wherein the duplex stainless steel comprises in weight % (wt %):

| | |
|---|---|
| C | max 0.030; |
| Si | max 0.8; |
| Mn | max 2.0; |
| Cr | 29.0 to 31.0; |
| Ni | 5.0 to 9.0; |
| Mo | less than 5.0; |
| W | less than 5.0; |
| N | 0.25 to 0.45; |
| Cu | max 2.0; |
| S | max 0.02; |
| P | max 0.03; | balance Fe and unavoidable occurring impurities; and
wherein the content of Mo+W is greater than 3.0 but less than 4.0.

Thus, e.g., the present disclosure relates to to the use in carbamate environment, such as ammonium carbamate environment, of the duplex stainless steel as defined hereinabove or hereinafter wherein the duplex stainless steel comprises in weight % (wt %):

| | |
|---|---|
| C | max 0.020; |
| Si | max 0.8; |
| Mn | max 2.0; |
| Cr | 29.0 to 31.0; |
| Ni | 5.0 to 9.0; |
| Mo | less than 5.0; |
| W | less than 5.0; |
| N | 0.25 to 0.45; |
| Cu | max 2.0; |
| S | max 0.01; |
| P | max 0.02; | balance Fe and unavoidable occurring impurities; and
wherein the content of Mo+W is greater than 3.0 but less than 4.0.

The inventors have come to the surprising finding that by manufacturing stripper tubes from the duplex stainless steel as defined hereinabove or hereinafter, the addition of oxygen to the process may be reduced to almost zero and still have a passive corrosion rate which is low in all parts of the urea plant also in the stripper tubes. Furthermore, the inventors have also found that conventionally used tests for assessing corrosion of stainless steel (such as the Streicher test with ferric sulfate-sulfuric acid test solution which are performed at 127° C.) which was used to develop the duplex stainless steel (as described in WO 95/00674) do not correlate with the actually observed corrosion in the specific equipment (stripper tube) in the urea plant. Therefore, the further improvement of the passive corrosion rate of the duplex stainless steel was only possible by corrosion tests in a high pressure autoclave simulating the actual process conditions which prevails in the specific equipment such as the stripper tubes.

The elementary composition of the duplex stainless steel is generally as defined hereinabove or hereinafter and the function of each alloying element is further described below.

Carbon (C) is to be considered as an impurity element in the present disclosure and has a limited solubility in both ferrite and austenite phase. This limited solubility implies that a risk for carbide precipitations exists at too high percentages, with decreased corrosion resistance as a consequence. Therefore, the C-content should be restricted to maximally 0.030 wt %, such as maximally 0.020 wt %, such as maximally 0.017 wt %, such as maximally 0.015 wt %, such as maximally 0.010 wt %.

Silicon (Si) is used as a deoxidation additive at steel manufacture. However, too high Si content increases the tendency for precipitations of intermetallic phases and decreases the solubility of N. For this reason the Si content should be restricted to max. 0.8 wt %, such as max 0.5 wt %, such as in the range of from 0.05 to 0.50 wt %, such as 0.1 to 0.5 wt %.

Manganese (Mn) is added to increase the solubility of N and for replacing Ni as an alloying element as Mn is considered to be austenite stabilizing. However, Mn may have a negative impact on the structure stability and therefore the content is max 2.0 wt %, such as max 1.5%, such as in the range of from 0.5 to 1.5 wt %.

Chromium (Cr) is the most active element for obtaining resistance against most types of corrosion. At urea synthesis, the Cr content is of great importance for the corrosion resistance, and should therefore be as high as possible. However, there is a balance between high chromium content and good structure stability. Therefore, in the present disclosure, in order to attain sufficient corrosion resistance and also ensure structural stability, the Cr content should be in the range of from 29.0 to 31.0 wt %. Hence, the Cr content is of from 29.0 to 31.0 wt %, such as of from 29.00 to 30.00 wt %.

Nickel (Ni) is mainly used as an austenite stabilizing element. The advantage with Ni is that it has no negative effect on the structure stability. A Ni content of at least 5.0 wt % is required to ensure the structural stability because if the Ni content is below 5 wt % chromium nitrides may be formed during heat treatment. However, Ni may form a strong complex with ammonium, therefore the Ni content should be kept as low as possible. Thus, the Ni content is in the range of from 5.0 to 9.0 wt %, such as from 5.5 to 8.5 wt %, such as from 5.5 to 7.5 wt. %.

Molybdenum (Mo) is used to improve the passivity of the duplex stainless steel. However, too high content of Mo involves the risk of precipitations of intermetallic phases. Therefore, Mo is less than 4.0 wt %. Tungsten (W) increases the resistance against pitting and crevice corrosion. However, too high content of W increases the risk for precipitation of intermetallic phases, particularly in combination with high contents of Cr and Mo. Therefore, W is less than 4.0 wt %. To obtain as good corrosion properties as possible, the content of Mo+W should be as high as possible without having the sensitivity for sigma phase unreasonable high. If the content of Mo+W is higher than 4.0 wt %, the driving force for sigma phase will be so high that it will be difficult to produce components without sigma phase. However, according to the present disclosure, it has shown that if W+Mo is higher than 3.0 wt %, the duplex stainless steel will have even less corrosion in the stripper tube. Thus, the Mo+W content is more than 3.0 wt % but less than 4.0 wt %. Furthermore, if the content of W+Mo is higher than 3.0 wt % but less than 4.0 wt %, then the duplex stainless steel as defined hereinabove or hereinafter contains a low amount of sigma phase, for example substantially no sigma phase, such as max. 0.5 wt %, such as max 0.05 wt %. The sigma phase should preferable be avoided as it will cause embrittlement in the duplex stainless steel and thereby reduce the corrosion resistance.

Nitrogen (N) is a strong austenite former and enhances the reconstitution of austenite. Additionally, N influences the distribution of Cr and Mo and Ni in the austenitic phase and ferritic phase. Thus, higher content of N increases the relative share of Cr and Mo in the austenitic phase. This means that the austenite becomes more resistant to corrosion, also that higher contents of Cr and Mo may be included into the duplex stainless steel while the structure stability is maintained. Hence, the N content should be at least 0.25 wt %. However, the solubility of nitrogen is limited and a too high level of nitrogen will increase the risk of forming chromium nitrides which in turn will affect the corrosion resistance. Therefore, N should not be more than 0.45 wt %. Thus, the N content is of from 0.25 to 0.45 wt %, such as of from 0.28 to 0.40 wt %.

Copper (Cu) is an optional element in the present disclosure and if included it will improve the general corrosion resistance in acid environments, such as sulfuric acid. However, high content of Cu will decrease the pitting and crevice corrosion resistance. Therefore, the content of Cu should be restricted to max. 2.0 wt %, such as max 1.0 wt %, such as max. 0.8 wt %.

Sulfur (S) influences the corrosion resistance negatively by the formation of easily soluble sulfides. Therefore, the content of S should be restricted to max. 0.02 wt. %, such as max. 0.01 wt %.

Phosphorus (P) is a common impurity element. If present in amounts greater than approximately 0.03 wt %, it can result in adverse effects on e.g. hot ductility, weldability and corrosion resistance. The amount of P in the alloy should be restricted to max 0.03 wt. %, such as max. 0.02 wt %.

When the term "max" is used, the skilled person knows that the lower limit of the range is 0 wt % unless another number is specifically stated. Hence for C, Si, Mn, Cu, S and P the lower limit is 0 wt %, as they are optional components.

Additionally, other elements may optionally be added to the duplex stainless steel as defined hereinabove or hereinafter during the manufacturing process in order to improve the processability, e.g. the hot workability, the machinability etc. Examples, but not limiting, of such elements are Ti, Nb, Hf, Ca, Al, Ba, V, Ce and B. If added, these elements are added in an amount of max 0.5 wt % in total. Optionally, e.g., it is possible for the alloy, as defined hereinabove or hereinafter, comprising the defined elements C, Si, Mn, Cr, Ni, Mo, W, N, Cu, S, and P in the amounts specified, with balance Fe+ unavoidable impurities, to consist of said defined elements in said amounts, plus max. 0.5 wt % of added optional elements, such as added for processability, such as Ti, Nb, Hf, Ca, Al, Ba, V, Ce and B, with balance Fe+ unavoidable impurities.

The balance in the duplex stainless steel as defined hereinabove or hereinafter is Fe and unavoidable impurities. Examples of unavoidable impurities are elements and compounds which have not been added on purpose, but cannot be fully avoided as they normally occur as impurities in e.g. the material used for manufacturing the duplex stainless steel.

The ferrite content of the duplex stainless steel according to the present disclosure is important for the corrosion resistance. Therefore, the ferrite content is preferably in the range of from 30% to 70% by volume, such as in the range of from 30 to 60 vol. %, such as in the range of from 30 to 55 vol. %, such as in the range of from 40 to 60 vol. %.

The duplex stainless steel as defined hereinabove or hereinafter may be manufactured according to conventional methods, i.e. casting followed by hot working and/or cold working and optional additional heat treatment. The duplex stainless steel as defined hereinabove or hereinafter may also be produced as a powder product by for example a hot isostatic pressure process (HIP).

The duplex stainless steel as defined hereinabove or hereinafter may be used for other applications, wherein good corrosion resistance is required for the equipment. Some examples of possible uses of the duplex stainless steel include use as a construction material in process chemistry components which are intended to be used in nitric acid environments, melamine production, use in the paper and pulp industry, such as in white liquor environment, and as welding wire material. The steel may be used for example for manufacturing seamless tubes, welded tubes, flanges, couplings and sheet-metal.

The present disclosure also relates to a formed object comprising the duplex stainless steel, according to one embodiment said object is a tube, such as for example a stripper tube for an urea production plant, or a liquid distributor for a stripper in a urea manufacturing plant. The present disclosure also relates to the use of a duplex stainless steel as defined hereinabove or hereinafter, in any one of the embodiments described hereinbefore and hereinafter, in a urea synthesis process. This use of the duplex stainless steel as defined hereinabove or hereinafter is for reducing corrosion of one or more parts of the equipment used in said process, such as of one or more parts of a high pressure urea synthesis section, such as of parts that come in contact with carbamate solution.

Yet a further aspect of the present disclosure is to provide a method for producing urea wherein at least one of the equipment parts, such as a part in contact with carbamate solution, is made from the duplex stainless steel as defined hereinabove or hereinafter. The carbamate solution may have an oxygen content of less than 0.1 ppm, such as less than 0.04 ppm (by weight).

Another aspect of the present disclosure is to provide a plant for the production of urea, wherein said plant comprises one or more parts comprising the duplex stainless steel as defined hereinabove or hereinafter. According to one embodiment, one or more of the stripper tubes comprises, or is made from, the duplex stainless steel as defined hereinabove or hereinafter. According to a further embodiment, the plant comprises a high pressure urea synthesis section comprising a stripper, wherein the stripper comprises at least one liquid distributor comprising the duplex stainless steel as defined hereinabove or hereinafter. Said duplex stainless steel can be used in a method of modifying an existing plant for the production of urea, said plant comprising one or more components selected from the group consisting of liquid distributors, radar cones, (control) valves and ejectors, wherein said method is characterized in that one or more stripper tubes are replaced by a stripper tube comprising the duplex stainless steel as defined hereinabove or hereinafter. The method can also be used in a method for reducing the corrosion rate of a urea plant by replacing at least one stripper tube with a stripper tube comprising the duplex stainless steel as defined hereinabove or hereinafter.

The present disclosure also involves the following numbered non-limiting embodiments:

Embodiment 1.0. Use of a duplex stainless steel in carbamate environment, the duplex stainless steel comprising in weight % (wt %):

| | |
|---|---|
| C | max 0.030; |
| Si | max 0.8; |
| Mn | max 2.0; |
| Cr | 29.0 to 31.0; |
| Ni | 5.0 to 9.0; |
| Mo | less than 4.0; |

-continued

| | |
|---|---|
| W | less than 4.0; |
| N | 0.25-0.45; |
| Cu | max 2.0; |
| S | max 0.02; |
| P | max 0.03; | balance Fe and unavoidable occurring impurities; and
wherein the content of Mo+W is greater than 3.0 but less than 4.0.

Embodiment 1.1. Use of a duplex stainless steel in carbamate environment, the duplex stainless steel comprising in weight % (wt %):

| | |
|---|---|
| C | max 0.020; |
| Si | max 0.8; |
| Mn | max 2.0; |
| Cr | 29.0 to 31.0; |
| Ni | 5.0 to 9.0; |
| Mo | less than 5.0; |
| W | less than 5.0; |
| N | 0.25 to 0.45; |
| Cu | max 2.0; |
| S | max 0.01; |
| P | max 0.02; | balance Fe and unavoidable occurring impurities; and
wherein the content of Mo+W is greater than 3.0 but less than 4.0.

Embodiment 1.2. Use of a duplex stainless steel according to embodiment 1.0 or 1.1, wherein Mn is of from 0.5-1.5 wt %.

Embodiment 1.3. Use of a duplex stainless steel according to embodiment 1.0, 1.1 or 1.2, wherein Si is of from 0.010 to 0.50 wt %.

Embodiment 1.4. Use of a duplex stainless steel according to any of embodiments 1.0 to 1.3, wherein Ni is of from 5.5 to 8.5 wt %, such as from 5.5 to 7.5 wt. %.

Embodiment 1.5. Use of a duplex stainless steel according to any of embodiments 1.0 to 1.4, wherein N is of from 0.28 to 0.40 wt %.

Embodiment 1.7. Use of a duplex stainless steel according to any one of embodiments 1.0-1.6 in a urea synthesis process for reducing corrosion of one or more parts of a high pressure urea synthesis section in contact with ammonium carbamate solution.

Embodiment 1.8 A formed object comprising the duplex stainless steel as defined in any one of Embodiments 1.0-1.6 wherein said formed object is a tube, a stripper tube for a plant for the production of urea or a liquid distributor for a stripper for a plant for production of urea.

Embodiment 1.9. A method for producing urea wherein at least one part of the equipment is made from a duplex stainless steel as defined in any one of embodiments 1.-0-1.6, the method preferably comprising forming ammonium carbamate, and dehydrating ammonium carbamate to provide urea.

Embodiment 1.10. A plant for the production of urea, wherein said plant comprising one or more parts comprising a duplex stainless steel as defined in any one of embodiments 1.0-1.6.

Embodiment 1.11 The plant according to embodiment 1.10, wherein said one or more parts is one or more stripper tubes.

Embodiment 1.12 The plant according to embodiments 1.10 or 1.11, comprising a high pressure urea synthesis section comprising a stripper, wherein the stripper comprises at least one liquid distributor comprising a duplex stainless steel as defined in any one of embodiments 1.0-1.6.

Embodiment 1.13. A method of modifying an existing plant for the production of urea, said plant comprising one or more components selected from the group consisting of liquid distributors, radar cones, (control) valves and ejectors, wherein said method is characterised in that one or more stripper tubes is replaced by a stripper tube comprising a duplex stainless steel as defined in any one of embodiments 1.0-1.6.

Embodiment 1.14. A method for reducing the passive corrosion rate of a urea plant by replacing at least one stripper tube with a stripper tube stripper comprising a duplex stainless steel as defined in any one of embodiments 1.1-1.6

Embodiment 2.0. A duplex stainless steel comprising in weight % (wt %):

| | |
|---|---|
| C | max 0.030; |
| Si | max 0.8; |
| Mn | max 2.0; |
| Cr | 29.0 to 31.0; |
| Ni | 5.0 to 9.0; |
| Mo | less than 4.0; |
| W | less than 4.0; |
| N | 0.25 to 0.45; |
| Cu | max 2.0; |
| S | max 0.02; |
| P | max 0.03; | balance Fe and unavoidable occurring impurities; and
wherein the content of Mo+W is greater than 3.0 but less than 4.0.

Embodiment 2.1. A duplex stainless steel comprising in weight % (wt %):

| | |
|---|---|
| C | max 0.020; |
| Si | max 0.8; |
| Mn | max 2.0; |
| Cr | 29.0 to 31.0; |
| Ni | 5.0 to 9.0; |
| Mo | less than 4.0; |
| W | less than 4.0; |
| N | 0.25 to 0.45; |
| Cu | max 2.0; |
| S | max 0.01; |
| P | max 0.02; | balance Fe and unavoidable occurring impurities; and
wherein the content of Mo+W is greater than 3.0 but less than 4.0.

Embodiment 2.2 The duplex stainless steel according to embodiment 2.0 or 2.1, wherein Mn is of from 0.5-1.5 wt %.

Embodiment 2.3. The duplex stainless steel according to embodiments 2.0, 2.1 or 2.2, wherein Si is of from 0.010 to 0.50 wt %.

Embodiment 2.4. The duplex stainless steel according to any of embodiments 2.0 to 2.3, wherein Ni is of from 5.5 to 8.5 wt %, such as from 5.5 to 7.5 wt. %.

Embodiment 2.5. The duplex stainless steel according to any of embodiments 2.0 to 2.4, wherein N is of from 0.28 to 0.40 wt %.

Embodiment 2.6.6. The duplex stainless steel according to embodiment 2.0, wherein Mn is of from 0.5-1.5 wt %, wherein Si is of from 0.010 to 0.50 wt %, wherein Ni is of from 5.5 to 8.5 wt % and wherein N is of from 0.28 to 0.40 wt %.

Embodiment 2.7. A formed object comprising the duplex stainless steel according to any of embodiments 2.0 to 2.6.

The present disclosure is further illustrated by the following non-limiting examples.

Examples

Table 1 shows the compositions of the duplex stainless steels used in the Examples. The objects used for testing were manufactured from 270 kg billets that were hot forged, hot rolled, cold rolled and then heat treated.

Corrosion Testing by Using Autoclaves

The samples were cut from 5 mm strips which were produced by hot warming to around 1200° C. and cold rolling (room temperature) with intermediate (around 1100° C.) and final annealing at 1070° C. The samples that were used for the tests had the form of coupons with the approximate dimensions 20×10×3 mm. All surfaces were machined and finished by wet grinding.

The corrosion resistance of the duplex stainless steel was evaluated in an oxygen-free carbamate solution. The composition of the carbamate solution was selected to simulate even worse conditions than normally prevailing in the stripper heat exchanger tubes in a urea plant. The temperature during the tests was 210° C. The corrosion rate was calculated after an exposure of 14 days in the oxygen-free carbamate solution. The results are shown in Table 3. As can be seen from the table, charges 1 and 2 have a better corrosion resistance than comparative charges 3-5 indicated by lower corrosion rate The following procedure was used for the exposures. The autoclave was carefully cleaned with ultrapure water and ethanol. The coupons (strips) were cleaned in acetone and ethanol and weighed and the dimensions of the coupons were measured. These were then mounted on a Teflon sample holder.

Water and urea were added to the autoclave. The autoclave was then purged with nitrogen to remove oxygen and other gases. Ammonia was then added to the autoclave.

Heating was initiated the following day, according to the temperature profile described in table 2. The sequence is designed to avoid over-shooting. The specimens were exposed for 14 days at 210° C.

TABLE 3

| Charge | Corrosion rate[mm/year] |
| --- | --- |
| 1 | 0.186 |
| 2 | 0.191 |
| 3 | 0.223 |
| 4 | 0.275 |
| 5 | 0.329 |

Mechanical Testing

The mechanical properties were evaluated by tensile testing, impact testing, and hardness measurements. 5 mm cold rolled and annealed strips were used for the tensile testing and hardness measurements. 11 mm hot rolled strips were used for the impact testing. The strips were manufactured as described above.

The tensile testing was performed at room temperature according to ISO6892-1:2009.

The impact testing specimens were standard V-notch test pieces (SSV1). The testing was performed according to ISO 14556. The tests were performed at two temperatures, room temperature and −35° C.

The hardness measurements were performed on the cross cut surface of the lengthwise samples taken from the 5 mm strip. The measurements were made in the center of the strip. Vickers hardness measurements were performed with a load of 10 kg (HV10).

The austenite spacing measurements were performed on the same specimens that were used for the hardness measurements. The measurements were performed in accordance with the recommended practice DNV-RP-F112, section 7 (October 2008).

The results of the mechanical testing are shown in the tables below:

TABLE 1

The composition of the charges of the examples

| Charge | C | Si | Mn | P | S | Cr | Ni | Mo | W | Mo + W | N | Cu |
| --- | --- | --- | --- | --- | --- | --- | --- | --- | --- | --- | --- | --- |
| 1 | 0.012 | 0.08 | 1 | 0.008 | 0.008 | 29.07 | 5.76 | 0.48 | 2.55 | 3.03 | 0.35 | 0.01 |
| 2 | 0.012 | 0.23 | 1.05 | 0.005 | 0.005 | 29.92 | 7.17 | 3.01 | — | 3.01 | 0.3 | — |
| 3 | 0.011 | 0.48 | 1.06 | 0.004 | 0.006 | 28.74 | 6.84 | 2.24 | — | 2.24 | 0.34 | <0.010 |
| 4 | 0.010 | 0.11 | 1.09 | 0.005 | 0.006 | 33.31 | 6.5 | 0.48 | — | 0.48 | 0.41 | <0.010 |
| 5 | 0.010 | 0.48 | 4.07 | 0.004 | 0.007 | 30.77 | 5.08 | 0.33 | — | 0.33 | 0.33 | <0.010 |

TABLE 2

Heating sequence of the autoclave.

| | Starting temp (° C.) | Final temp (° C.) | Heating rate (° C./min) |
| --- | --- | --- | --- |
| 1 | RT | 195 | 1 |
| 2 | 195 | 208 | 0.2 |
| 3 | 208 | 210 | 0.1 |

TABLE 4A

Results from tensile testing

| Charge | Rp0.2 (MPa) | Rp0.1 (MPa) | Rm (MPa) | A (%) |
| --- | --- | --- | --- | --- |
| 1 | 626 | 717 | 865 | 30 |
| 2 | 648 | 744 | 878 | 27 |

TABLE 4A-continued

Results from tensile testing

| Charge | Rp0.2 (MPa) | Rp0.1 (MPa) | Rm (MPa) | A (%) |
| --- | --- | --- | --- | --- |
| 3 | 566 | 669 | 831 | 31 |
| 4 | 669 | 755 | 883 | 28 |
| 5 | 617 | 703 | 817 | 28 |

TABLE 4B

Results from impact testing RT

| Charge | RT-1 | RT-2 | RT-3 |
|---|---|---|---|
| 1 | 146 | 169 | 153 |
| 2 | 194 | 188 | 178 |
| 3 | 202 | 208 | 213 |
| 4 | 172 | 178 | 178 |
| 5 | 143 | 135 | 150 |

TABLE 4C

Results from impact testing −35° C.

| Charge | Test 1 (J) | Test 2 (J) | Test 3 (J) | Average (J) |
|---|---|---|---|---|
| 1 | 107 | 146 | 130 | 128 |
| 2 | 145 | 141 | 137 | 141 |
| 3 | 165 | 179 | 186 | 177 |
| 4 | 37 | 40 | 39 | 39 |
| 5 | 24 | 23 | 20 | 22 |

TABLE 4D

Result of the hardness testing

| | HV10 | | | |
|---|---|---|---|---|
| Charge | Indent 1 | Indent 2 | Indent 3 | Average |
| 1 | 309 | 283 | 285 | 292 |
| 2 | 292 | 292 | 283 | 289 |
| 3 | 285 | 285 | 292 | 287 |
| 4 | 279 | 292 | 297 | 289 |
| 5 | 266 | 276 | 281 | 274 |

TABLE 4E

Result of the austenite spacing
Austenite spacing (μm)

9.7
12.1
4.5

TABLE 4E-continued

Result of the austenite spacing
Austenite spacing (μm)

9
12.2

What is claimed is:

1. A duplex stainless steel, having a composition consisting of in weight % (wt %):
C 0.010 to 0.015;
Si 0.08 to 0.23;
Mn 1.0 to 1.05;
Cr 29.07 to 29.92;
Ni 5.76 to 7.17;
Mo 3.0 to 4.0;
N 0.3 to 0.35;
S max 0.008;
P max 0.008;
at least one of Ti, Nb, Hf, Ca, Ba, V, and B max 0.5 total; and
balance Fe and unavoidable occurring impurities,
wherein sigma phase is max 0.5 wt %,
wherein the duplex stainless steel has an austenite spacing of 1.2 microns,
wherein the duplex stainless steel has a corrosion rate of 0.191 mm/year,
wherein the corrosion rate is evaluated on a sample of the duplex stainless steel in an oxygen-free carbamate solution at a temperature of 210° C. for 14 days, and
wherein the sample is in the form of a coupon having dimensions of 20×10×3 mm obtained from a 5 mm strip produced by hot warming to 1200° C. and cold rolling at room temperature with intermediate annealing at 1100° C. and final annealing at 1070° C., and surfaces of the sample were machined and finished by wet grinding.

2. The duplex stainless steel according to claim 1, wherein sigma phase is max 0.05 wt %.

3. The duplex stainless steel according to claim 1, wherein the duplex stainless steel is substantially free of intermetallic phase.

4. A formed object, comprising the duplex stainless steel according to claim 1.

5. The formed object according to claim 4, wherein said formed object is a tube.

* * * * *